(12) United States Patent
Takaoka et al.

(10) Patent No.: US 8,214,025 B2
(45) Date of Patent: Jul. 3, 2012

(54) FLUORESCENCE ENDOSCOPE SYSTEM

(75) Inventors: Hideyuki Takaoka, Tokyo (JP); Koki Morishita, Tokyo (JP)

(73) Assignee: Olympus Corporation, Tokyo (JP)

( * ) Notice: Subject to any disclaimer, the term of this patent is extended or adjusted under 35 U.S.C. 154(b) by 404 days.

(21) Appl. No.: 12/521,201

(22) PCT Filed: Dec. 27, 2007

(86) PCT No.: PCT/JP2007/075189
§ 371 (c)(1),
(2), (4) Date: Jun. 25, 2009

(87) PCT Pub. No.: WO2008/081897
PCT Pub. Date: Jul. 10, 2008

(65) Prior Publication Data
US 2010/0016669 A1 Jan. 21, 2010

(30) Foreign Application Priority Data
Dec. 28, 2006 (JP) .................................. 2006-356140

(51) Int. Cl.
*A61B 1/00* (2006.01)
(52) U.S. Cl. ....................................... 600/478; 600/160
(58) Field of Classification Search .................. 600/160, 600/478
See application file for complete search history.

(56) References Cited

U.S. PATENT DOCUMENTS

| 6,293,911 | B1 | 9/2001 | Imaizumi et al. | |
|---|---|---|---|---|
| 2004/0186351 | A1 | 9/2004 | Imaizumi et al. | |
| 2005/0065440 | A1* | 3/2005 | Levenson | 600/476 |
| 2006/0247535 | A1 | 11/2006 | Sendai | |
| 2006/0247537 | A1 | 11/2006 | Matsumoto | |
| 2007/0016078 | A1* | 1/2007 | Hoyt et al. | 600/476 |
| 2008/0015446 | A1* | 1/2008 | Mahmood et al. | 600/476 |

FOREIGN PATENT DOCUMENTS

| JP | HEI-10-201707 | 8/1998 |
|---|---|---|
| JP | 2006-221107 | 8/2006 |
| JP | 2006-263044 | 10/2006 |
| JP | 2006-296635 | 11/2006 |

* cited by examiner

*Primary Examiner* — Jonathan Cwern
(74) *Attorney, Agent, or Firm* — Scully, Scott, Murphy & Presser, P.C.

(57) ABSTRACT

Provided is a fluorescence endoscope system for observing fluorescence from a fluorochrome attached to or absorbed in biological tissue, including an excitation light source that emits excitation light that excites the fluorochrome; an image-acquisition section that acquires fluorescence emitted from the biological tissue when irradiated with the excitation light from the excitation light source; an autofluorescence signal setting section that sets an autofluorescence signal intensity to be emitted from the biological tissue when irradiated with the excitation light; and an image compensation section that compensates fluorescence image information acquired by the image-acquisition section on the basis of the autofluorescence signal intensity set by the autofluorescence signal setting section.

6 Claims, 8 Drawing Sheets

FLUORESCENCE ENDOSCOPE SYSTEM

TECHNICAL FIELD

The present invention relates to a fluorescence endoscope system.

BACKGROUND ART

Heretofore, certain kinds of proteins etc. are known to be over-expressed in cancer cells compared with normal parts. Therefore, methods have been proposed that diagnose cancer cells, using a fluorescent probe (agent), by shining light on the expressed protein molecules and that distinguish cancer cells by endoscopic observation of the fluorescence due to the fluorescent probe (for example, see Patent Document 1).

Patent Document 1 discloses an endoscope apparatus for diagnosing cancer cells using one type of fluorescent probe.
Patent Document 1: Japanese Unexamined Patent Application, Publication No. HEI-10-201707

DISCLOSURE OF INVENTION

The present invention provides a fluorescence endoscope system that can suppress the influence of autofluorescence and that can accurately and clearly distinguish abnormal tissue, such as cancer cells, with a clear fluorescence image based on fluorescence emitted from a fluorescent probe.

The present invention provide a fluorescence endoscope system for observing fluorescence from a fluorochrome attached to or absorbed in biological tissue, comprising:

an excitation light source that emits excitation light that excites the fluorochrome;

an image-acquisition section that acquires fluorescence emitted from the biological tissue when irradiated with the excitation light from the excitation light source;

an autofluorescence signal setting section that sets an autofluorescence signal intensity to be emitted from the biological tissue when irradiated with the excitation light; and an image compensation section that compensates fluorescence image information acquired by the image-acquisition section on the basis of the autofluorescence signal intensity set by the autofluorescence signal setting section.

In the above-described invention, the autofluorescence signal setting section may include an image region specifying section that specifies an image region in at least part of the fluorescence image acquired by the image-acquisition section, and a fluorescence signal intensity in the image region specified by the image region specifying section may be set as the autofluorescence signal intensity.

The above-described invention may further include another excitation light source that emits other excitation light in a wavelength band in which the excitation efficiency of the fluorochrome is lower than with the excitation light, in a wavelength band different from the excitation light emitted from the excitation light source, wherein when the two kinds of excitation light are radiated from the two excitation light sources in an alternating manner, the image-acquisition section may acquire the respective fluorescences emitted from the biological tissue, and the autofluorescence signal setting section may estimate the autofluorescence signal intensity on the basis of the fluorescence image information acquired by the image-acquisition section when the other excitation light is radiated.

The above-described invention may further include a reference light source that emits illumination light for acquiring a reflection-light image from the biological tissue; wherein when excitation light from the excitation light source and reference light from the reference light source are radiated in an alternating manner, the image-acquisition section may acquire the fluorescence emitted from the biological tissue and the reflected light of the reference light, respectively, and the autofluorescence signal setting section may estimate the autofluorescence signal intensity on the basis of reflection-image information acquired by the image-acquisition section when the reference light is radiated.

In the above-described invention, the reference light source may be formed of the excitation light source.

EXPLANATION OF REFERENCE SIGNS

1, 20, 30: fluorescence endoscope system
3: image-acquisition unit (image-acquisition section)
4: light source unit (excitation light source)
4a, 4b: excitation light source (excitation light source)
4b': reference light source (reference light source)
5 autofluorescence signal setting section
6 image compensation section 13: cursor-position setting section (image region specifying section)

BEST MODE FOR CARRYING OUT THE INVENTION

An endoscope system 1 according to a first embodiment of the present invention will be described below with reference to FIG. 1 and FIGS. 2A to 2D.

Figure 1:
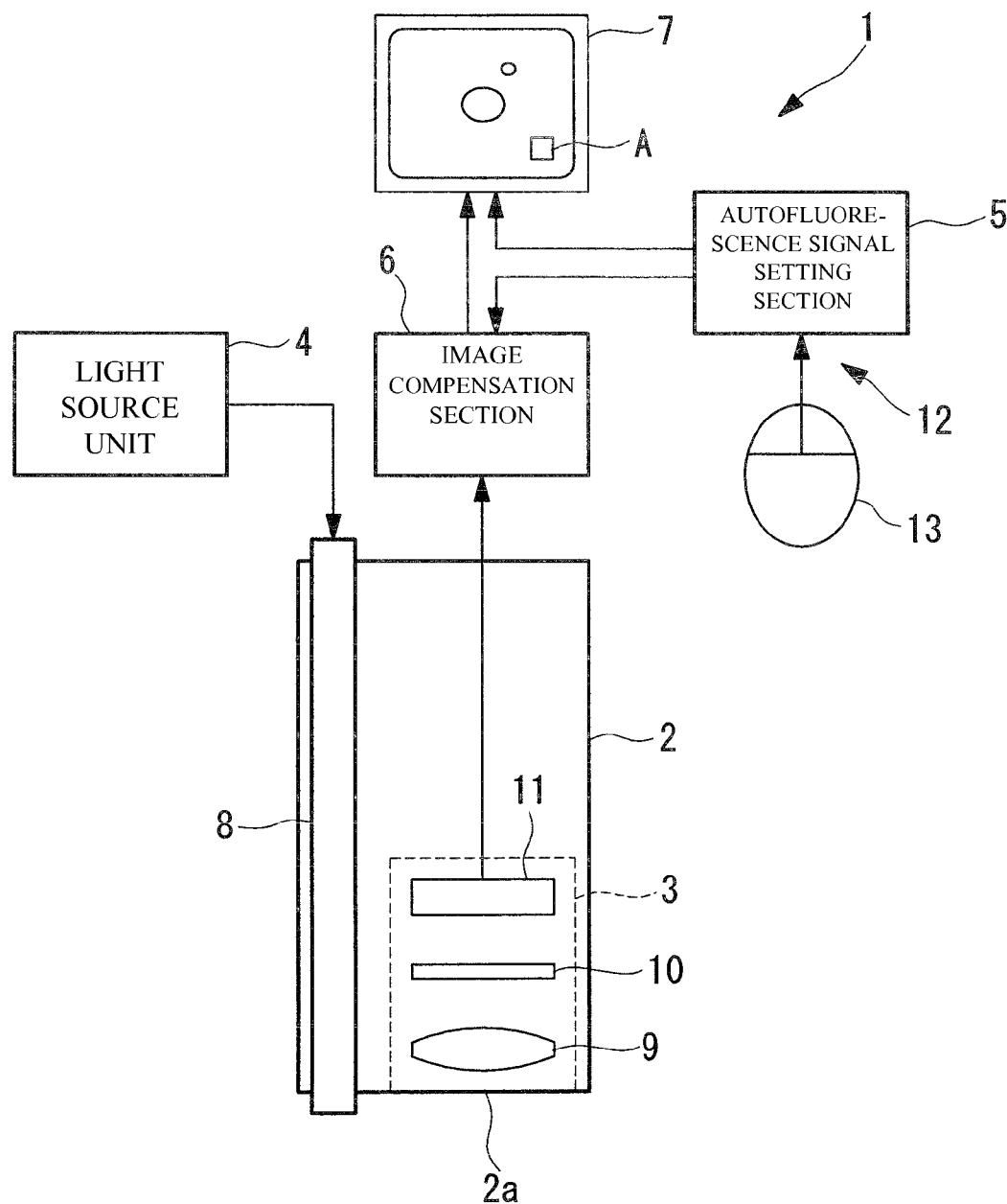
FIG. 1 is a diagram showing the overall configuration of a fluorescence endoscope system according to a first embodiment of the present invention.

As shown in FIG. 1, the fluorescence endoscope system 1 according to this embodiment includes an insertion section 2 to be inserted inside the body cavity of a living organism, an image-acquisition unit (image-acquisition section) 3 disposed inside the insertion section 2, a light-source unit 4 that emits excitation light, an autofluorescence signal setting section 5 that sets the signal intensity of autofluorescence to be emitted from biological tissue when irradiated with the excitation light from the light source unit 4, an image compensation section 6 that performs compensation on the basis of the autofluorescence signal intensity set by the autofluorescence signal setting section 5, and a display unit 7 that displays fluorescence image information acquired by the image-acquisition unit 3 and fluorescence image information compensated by the image compensation section 6.

The insertion section 2 has extremely thin outer dimensions allowing it to be inserted in the body cavity of the living organism. The insertion section 2 is provided, in the interior thereof, with the image-acquisition unit 3 and a light guide 8 through which light from the light-source unit 4 propagates to a tip 2a.

The image-acquisition unit 3 includes an objective lens 9 that collects light incident from the object under observation, a fluorescence filter 10 that transmits fluorescence in a specific wavelength band in the light collected by the objective lens 9, and an image-acquisition device 11 that acquires the fluorescence transmitted through the fluorescence filter 10 and converts it to an electrical signal.

The autofluorescence signal setting section 5 includes an image-region specifying section 12 that specifies an image region in at least part of the fluorescence image acquired by the image-acquisition unit 3. The image-region specifying section includes a cursor display section (not shown in the drawing) that displays on the screen of the display unit 7 a cursor A for specifying a specific image region and a cursor-position setting portion 13, such as a mouse, that causes the cursor A displayed by the cursor display section to move on the screen of the display unit 7. The autofluorescence signal setting section 5 obtains intensity information of the fluorescence image inside the cursor A on the display unit 7, specified by the cursor-position setting section 13, to calculate the average value thereof, and sets the calculated average intensity as autofluorescence intensity information.

The image compensation section 6 receives the fluorescence image information acquired by the image-acquisition device 11 and the autofluorescence intensity information set by the autofluorescence signal setting section 5, subtracts the autofluorescence intensity set by the autofluorescence signal setting section 5 from the intensity of each pixel in the fluorescence image information, and outputs it to the display unit 7.

The operation of the thus-configured fluorescence endoscope system 1 according to this embodiment will be described below.

To observe biological tissue having a fluorescent agent attached thereto or absorbed therein using the fluorescence endoscope system 1 according to this embodiment, first the insertion portion 2 is inserted inside the body cavity and the tip 2a thereof is made to face an observation site inside the body cavity. When excitation light is emitted from the light-source unit 4 in this state, the excitation light propagated through the light guide 8 radiates the observation site inside the body cavity.

The fluorescent agent attached to or absorbed in the biological tissue is excited upon irradiation with the excitation light, and agent fluorescence is emitted. And the autofluorescent material that the biological tissue naturally contains is also excited upon irradiation with the excitation light. This agent-fluorescence and autofluorescence light in a specific wavelength band is transmitted through the fluorescence filter 10 and is acquired by the image-acquisition device 11.

Accordingly, fluorescence image information that contains both agent-fluorescence and autofluorescence is acquired by the image-acquisition device 11. Then, the fluorescence image information acquired by the image-acquisition device 11 is sent to the image compensation section 6 and is also output to the display unit 7 via the image compensation section 6 for display.

In this state, the observer operates the cursor-position setting section 13 while observing the fluorescence image displayed on the display unit 7, thereby moving the cursor A in the fluorescence image to specify a region considered to be normal tissue (in other words, a region considered not to have the fluorescent agent attached thereto or absorbed therein). Once the image region in the fluorescence image is specified by the observer, fluorescence image information in that specified image region is sent to the autofluorescence signal setting section 5. Thus, an average value of the fluorescence intensity in the image region is calculated in the autofluorescence signal setting section 5 and is output to the image compensation section 6 as autofluorescence intensity information.

Figure 2A:
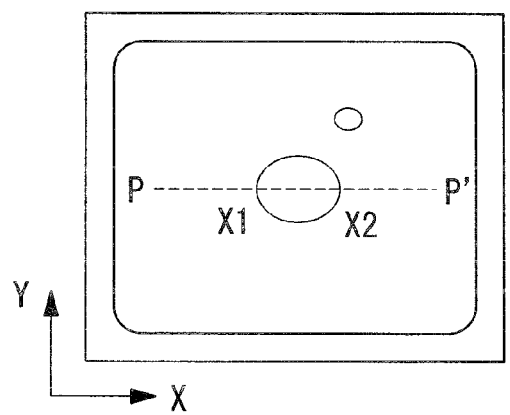
FIG. 2A is an example of a fluorescence image acquired by the fluorescence endoscope system in FIG. 1.
Figure 2B:
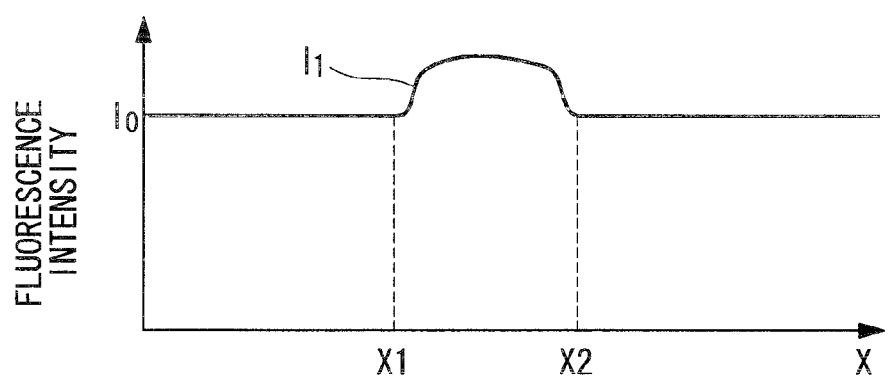
FIG. 2B is a diagram showing a fluorescence intensity distribution along line P-P' in the fluorescence image in FIG. 2A.

The fluorescence image information sent from the image-acquisition device 11 and the autofluorescence intensity information sent from the autofluorescence signal setting section 5 are received in the image compensation section 6, and the autofluorescence intensity information is subtracted from the fluorescence image information. In other words, as shown in FIGS. 2A and 2B, the fluorescence image information sent from the image-acquisition device 11 contains both agent-fluorescence intensity information $I_1$ and autofluorescence intensity information $I_0$. It should be noted that each of symbols X1 and X2 indicate a boundary between an autofluorescence and an agent fluorescence in a fluorescence intensity distribution along line P-P'.

Figure 2C:
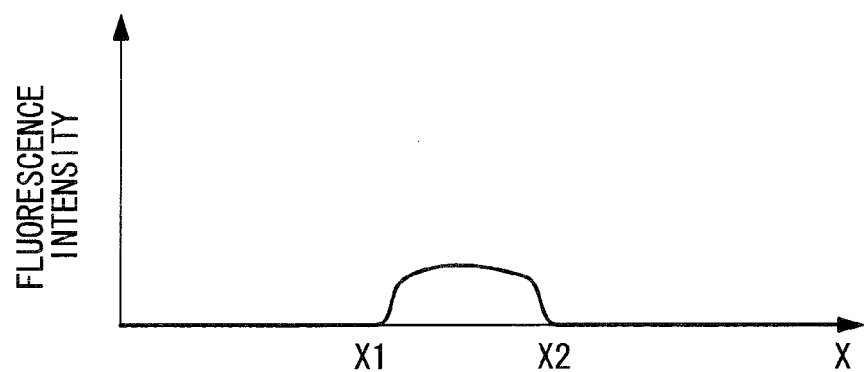
FIG. 2C is a fluorescence intensity distribution along line P-P' after compensation of the fluorescence image in FIG. 2A.
Figure 2D:
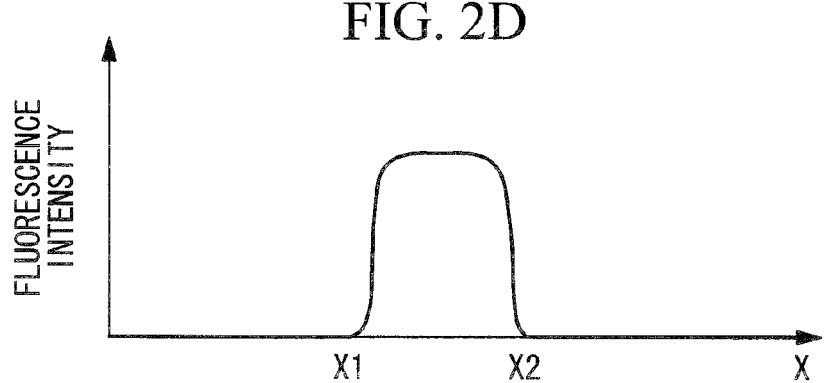
FIG. 2D is a fluorescence intensity distribution along line P-P' after amplification of the fluorescence image in FIG. 2A.
Figure 3:
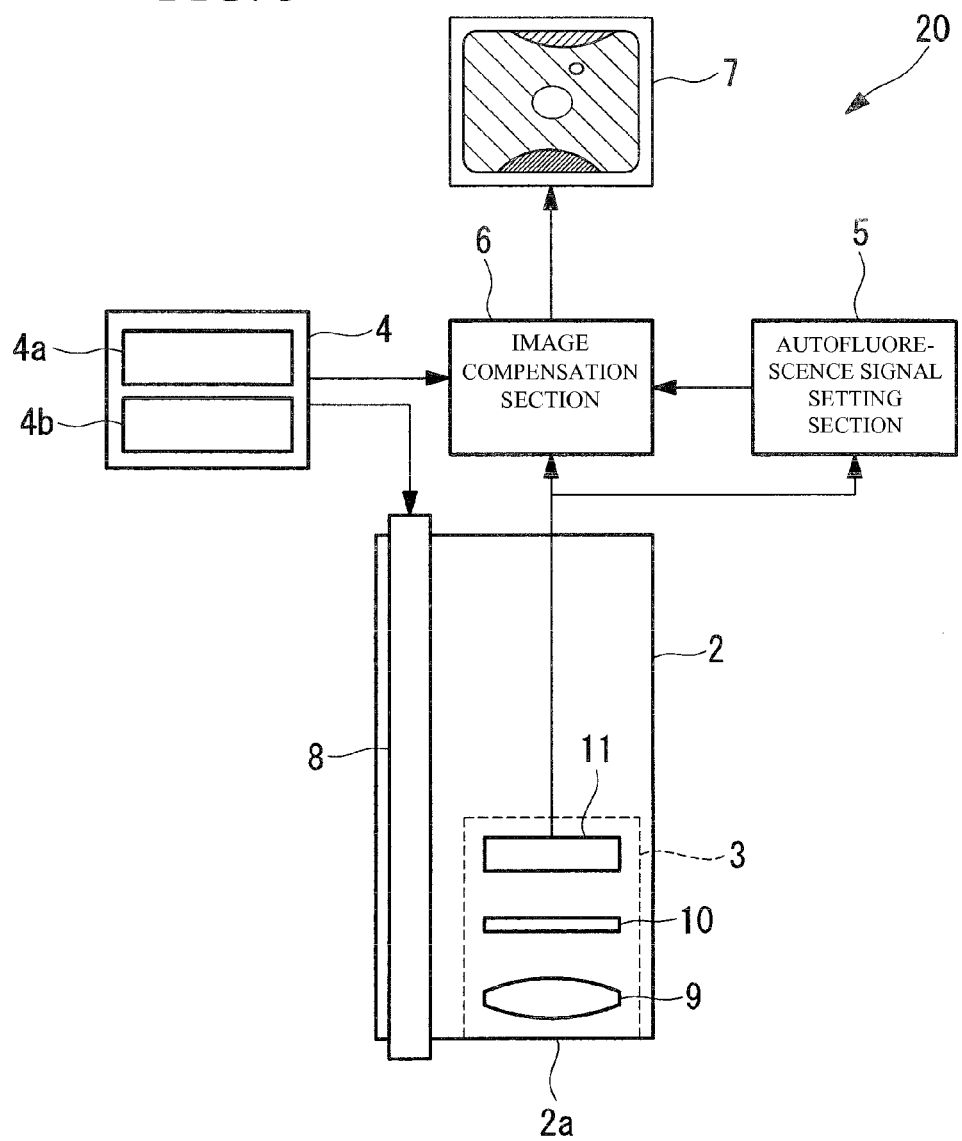
FIG. 3 is a diagram showing the overall configuration of a fluorescence endoscope system according to a second embodiment of the present invention.

Hence, as shown in FIG. 2C, by subtracting the autofluorescence intensity information $I_0$ from the agent-fluorescence intensity information $I_1$ in the image compensation section 6, it is possible to reduce background fluorescence the fluorescence in a region other than the region where the agent fluorescence is produced (background fluorescence). Thus, the fluorescence endoscope system 1 according to this embodiment is advantageous in that it is possible to improve the contrast of the image of the fluorescence agent, thus obtaining a clear fluorescence image. Additionally, as shown in FIG. 2D, by performing amplification processing after subtraction, it is possible to obtain a fluorescence image having further improved contrast.

In this embodiment, a mouse is given as an example of the cursor-position setting section 13. Instead of this, however, as the cursor-position setting section 13, it is also possible to use another device, such as a touch pen, or to input coordinates as numeric values.

In this embodiment, the average value of the fluorescence intensity in the image region specified on the display unit 7 with the cursor A is calculated and used as the autofluorescence intensity information $I_0$. Instead of this, the observer can manually input any value as the autofluorescence intensity information $I_0$, and to subtract this.

Next, a fluorescence endoscope system 20 according to a second embodiment of the present invention will be described below with reference to FIGS. 3 and 4 and FIGS. 5A to 5D.

In the description of this embodiment, parts having the same configuration as those of the fluorescence endoscope system 1 according to the first embodiment described above are assigned the same reference numerals, and a description thereof will be omitted.

The fluorescence endoscope system 20 according to this embodiment differs from the fluorescence endoscope system 1 according to the first embodiment in that the light-source unit 4 is provided with two types of excitation light sources 4a and 4b that emit excitation light in two different wavelength bands, and in that the autofluorescence signal setting section 5 estimates autofluorescence intensity information on the basis of fluorescence image information acquired by the image-acquisition device 11.

Figure 4:
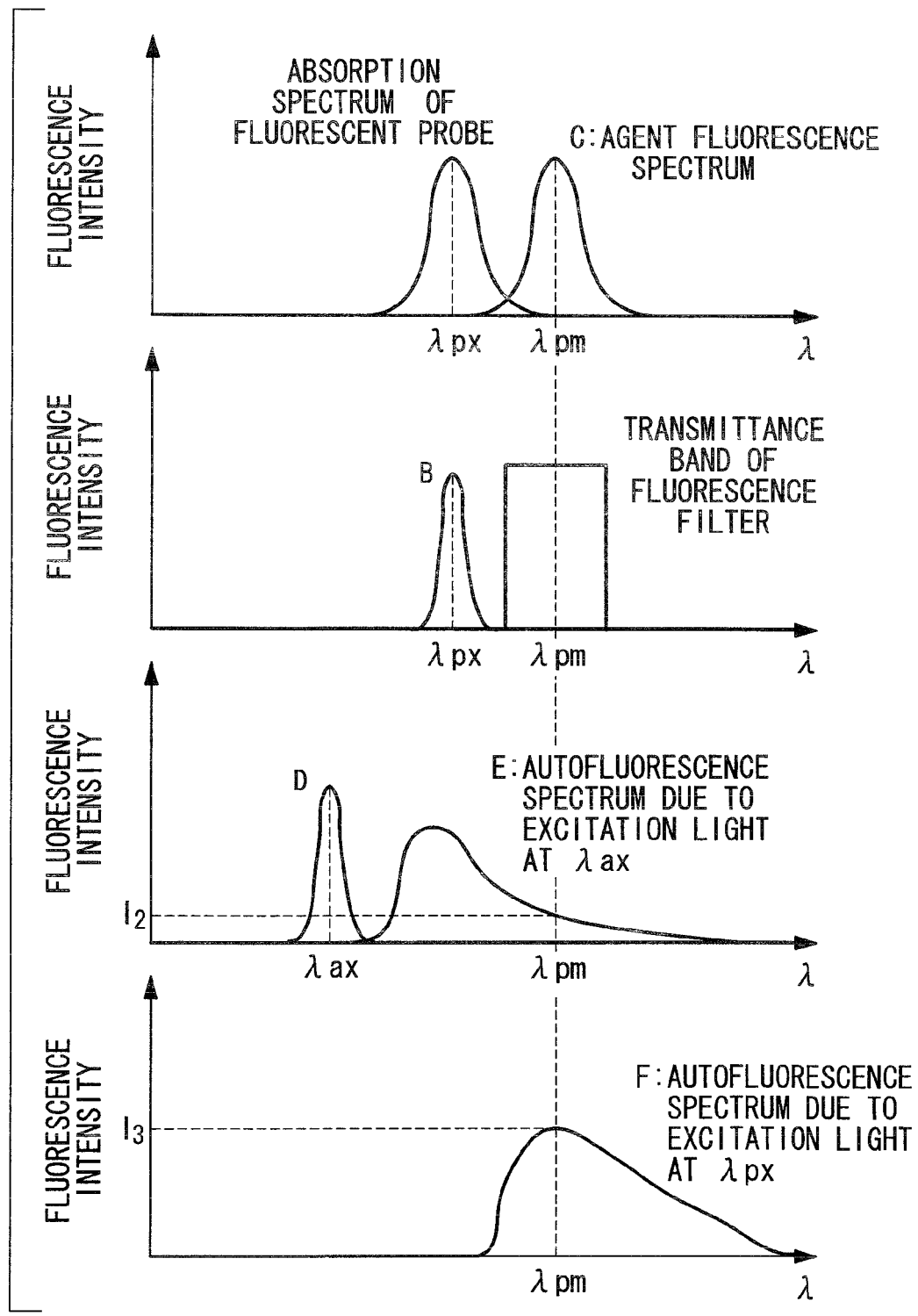
FIG. 4 is a diagram showing wavelength characteristics of an excitation light source, agent-fluorescence, autofluorescence, and a fluorescence filter in the fluorescence endoscope system in FIG. 3.

FIG. 4 shows a spectrum B of a first excitation light source 4a provided in the light-source unit 4, a spectrum C of agent-fluorescence excited by the excitation light from the first excitation light source 4a, a spectrum D of a second excitation light source 4b, a spectrum E of autofluorescence excited by the excitation light from the second excitation light source 4b, and a spectrum F of autofluorescence excited by the excitation light from the first excitation light source 4a. The excitation light from the second excitation-light source 4b has a wavelength band in which the excitation efficiency of the fluorescent agent attached to or absorbed in the biological tissue is sufficiently low compared with that of the excitation light from the first excitation light source 4a.

The autofluorescence signal setting section 5 calculates and stores, in advance, a ratio $\alpha$ $(=I_2/I_3)$ between the autofluorescence intensity $I_2$ emitted from the biological tissue when irradiated with the excitation light from the first excitation light source 4a and an autofluorescence intensity $I_3$ emitted from the biological tissue when irradiated with the excitation light from the second excitation light source 4b, in a state where the fluorescent agent is not dispersed. Then, during fluorescence observation in a state where the fluorescent agent is dispersed, it calculates the autofluorescence intensity information when the excitation light is radiated from the first excitation light source 4a by multiplying the fluorescence information obtained by radiating the excitation light from the second excitation light source 4b by the previously stored ratio $\alpha$.

The operation of the thus-configured fluorescence endoscope system 20 according to this embodiment will be described below.

To observe biological tissue having the fluorescent agent attached thereto or absorbed therein using the fluorescence endoscope system 20 according to this embodiment, first, the insertion section 2 is inserted into the body cavity, and the tip 2a thereof is made to face an observation site inside the body cavity. In this state, excitation light is emitted from both the first and second excitation light sources 4a and 4b in the light-source unit 4, and the two kinds of excitation light propagated through the light guide 8 are radiated onto the observation site in the body cavity in an alternating manner.

The fluorescent agent attached to or absorbed in the biological tissue is excited upon irradiation with the excitation light from the first excitation light source 4a, and agent fluorescence is emitted. The autofluorescent material that the biological tissue naturally contains is also excited upon irradiation with the same excitation light. This agent-fluorescence and autofluorescence light in a specific wavelength band is transmitted through the fluorescence filter 10 and is acquired by the image-acquisition device 11. Accordingly, an image containing intensity information of the agent-fluorescence (hereinafter called agent-fluorescence image information) is obtained.

The excitation light from the second excitation light source 4b is light in a wavelength band in which the excitation efficiency of the fluorescent probe is sufficiently low compared with that of the excitation light from the first excitation light source 4a; therefore, the agent-fluorescence is small even though the excitation light from this second excitation light source 4b is radiated, and autofluorescence is exclusively emitted. Of the autofluorescence emitted from the biological tissue, light in a specific wavelength band is transmitted through the fluorescence filter 10 and is acquired by the image-acquisition device 11. Accordingly, an image containing intensity information of the autofluorescence (hereinafter referred to as autofluorescence image information) is obtained.

Then, by sending the autofluorescence image information acquired by the image-acquisition device 11 to the autofluorescence signal setting section 5, it is multiplied by the ratio $\alpha$ that was stored in advance, and the autofluorescence intensity information is estimated. The estimated autofluorescence intensity information is sent to the image compensation section 6.

Figure 5A:
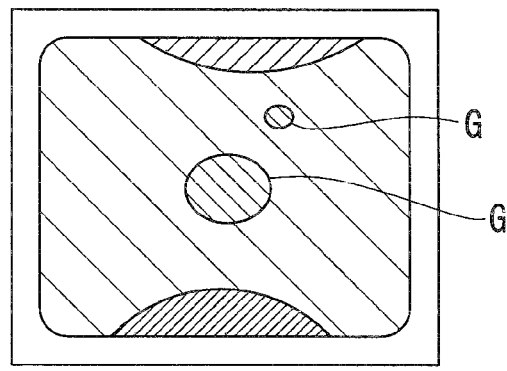
FIG. 5A is an example of a fluorescence image containing agent-fluorescence and autofluorescence, acquired by the fluorescence endoscope system in FIG. 1.
Figure 5B:
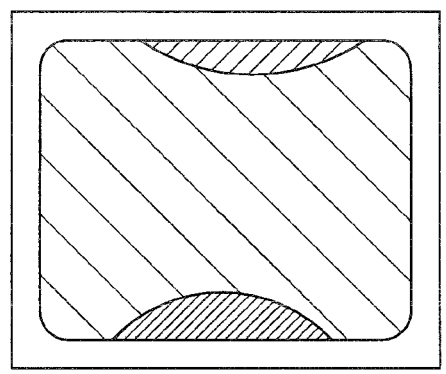
FIG. 5B is an example of an autofluorescence image acquired by the fluorescence endoscope system in FIG. 1.
Figure 5C:
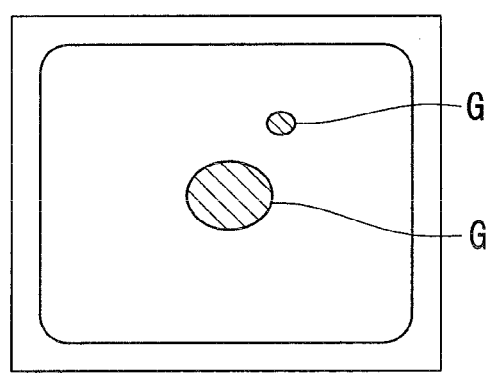
FIG. 5C is a diagram showing an example of an agent-fluorescence image after compensation, acquired by the fluorescence endoscope system in FIG. 1.

Similarly to the first embodiment, the agent-fluorescence image information acquired by the image-acquisition device 11 and the autofluorescence intensity information calculated by the autofluorescence signal setting section 5 are input to the image compensation section 6, where the autofluorescence intensity information is subtracted from the agent-fluorescence image information. In other words, as shown in FIG. 5A, both agent-fluorescence and autofluorescence are contained in the fluorescence image information sent from the image-acquisition device 11. Therefore, in the image compensation section 6, by subtracting the autofluorescence intensity information estimated in the autofluorescence signal setting section 5, such as that shown in FIG. 5B, it is possible to reduce the fluorescence (background fluorescence) in regions other than a region G where agent-fluorescence is produced, as show in FIG. 5C. Thus, with the fluorescence endoscope system 20 according to this embodiment, it is possible to improve the contrast of the image of the agent-fluorescence, thus obtaining a clear fluorescence image.

In particular, in this embodiment, unlike the first embodiment in which the autofluorescence intensity information is subtracted indiscriminately, the autofluorescence intensity information estimated on the basis of the actually acquired autofluorescence image of the biological tissue is subtracted. Accordingly, it is possible to subtract autofluorescence intensity information in consideration of intensity variations in the image caused by the elements of the endoscope system 20, such as the light source, the optical system, and the image-acquisition device 11, as well as intensity variations in the image caused by undulations in the biological tissue or the distance from the tip 2a of the insertion section 2. As a result, there is an advantage in that it is possible to more reliably remove background fluorescence, allowing observation with a clearer agent-fluorescence image.

Next, a fluorescence endoscope system 30 according to a third embodiment of the present invention will be described below with reference to FIGS. 6 and 7.

In the description of this embodiment, parts having the same configuration as those in the fluorescence endoscope system 20 according to the second embodiment described above are assigned the same reference numerals, and a description thereof will be omitted.

Figure 6:
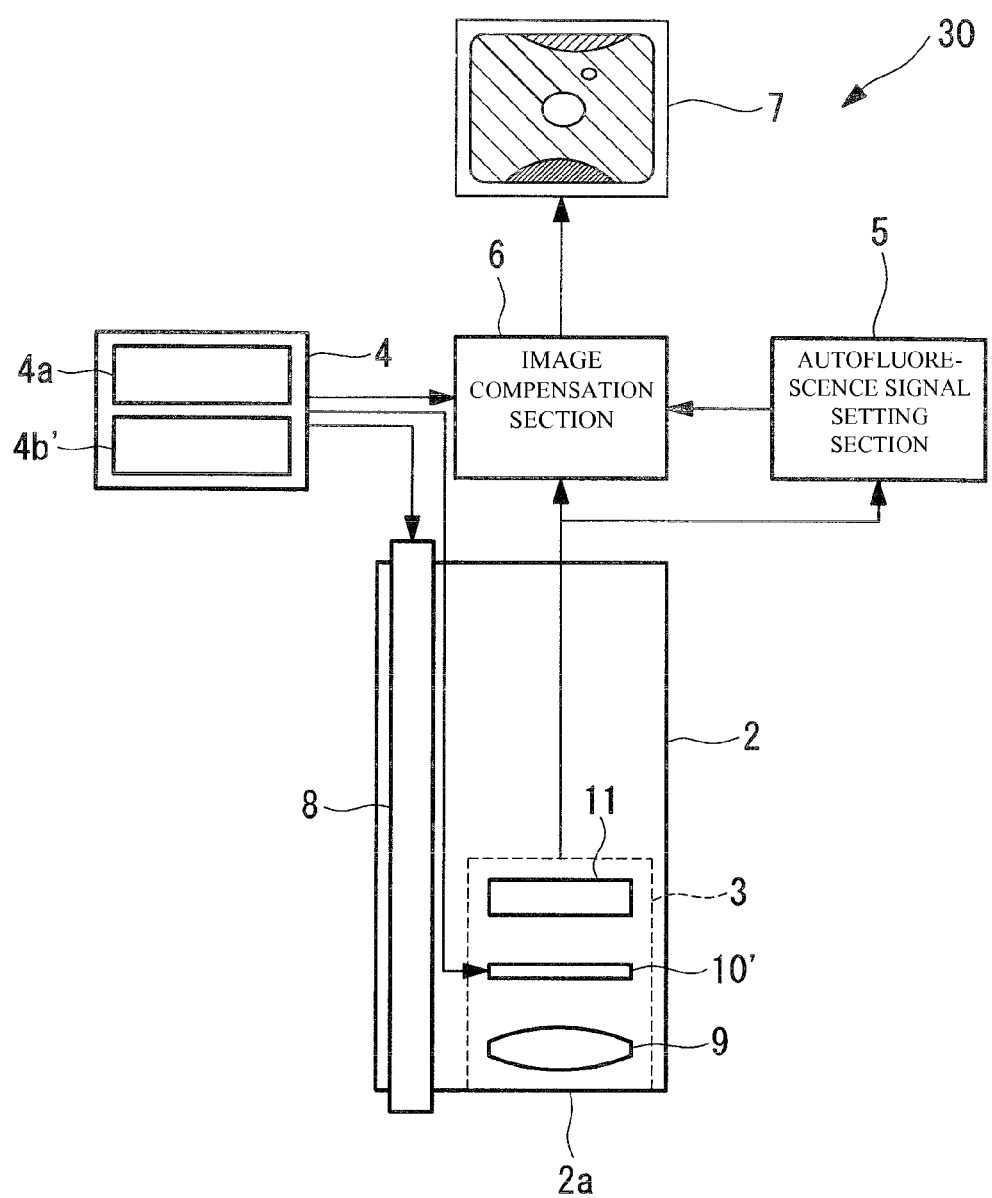
FIG. 6 is a diagram showing the overall configuration of a fluorescence endoscope system according to a third embodiment of the present invention.
Figure 7:
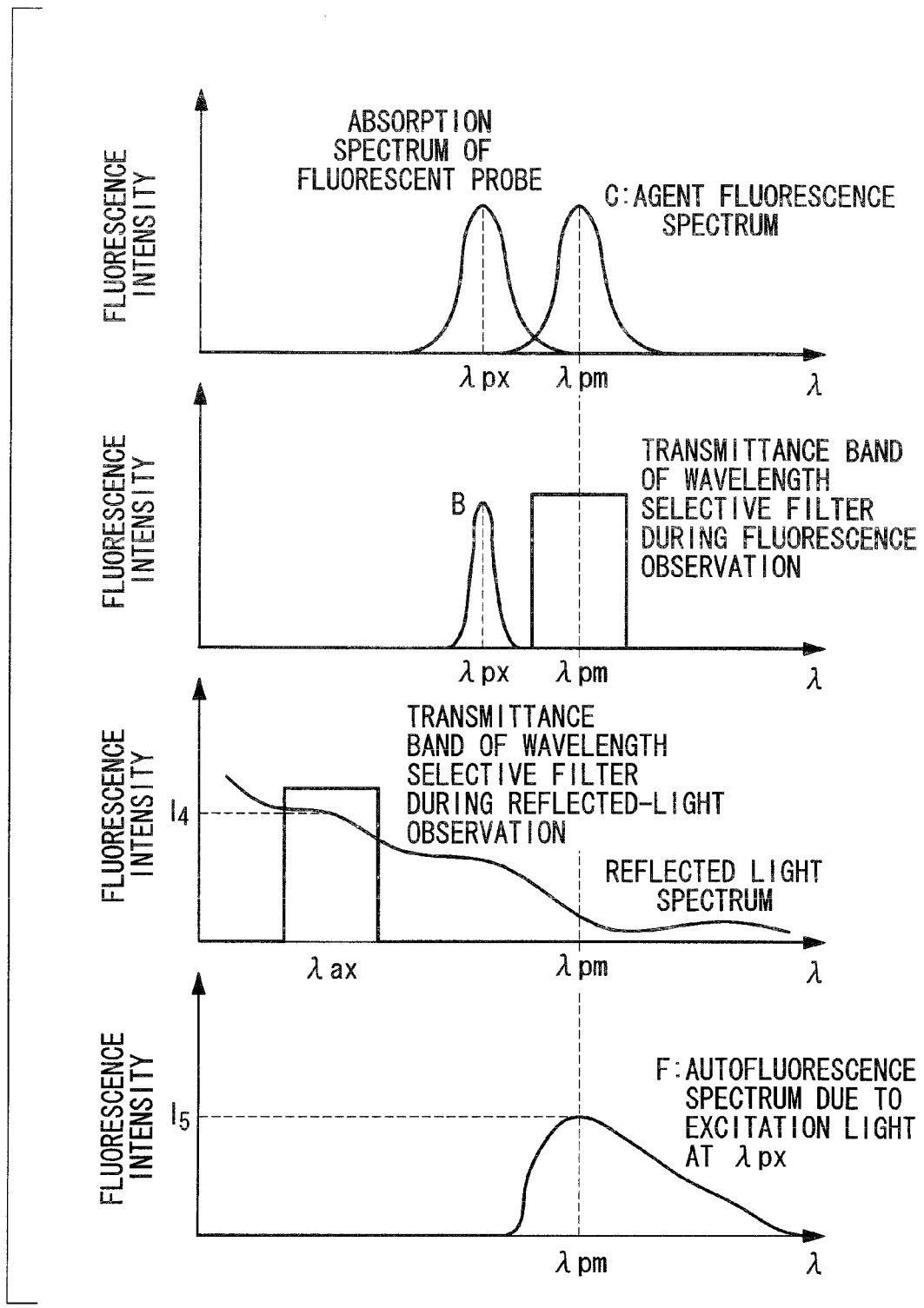
FIG. 7 is a diagram showing wavelength characteristics of an excitation light source, agent-fluorescence, autofluorescence, and a fluorescence filter in the fluorescence endoscope system in FIG. 3.

As show in FIG. 6, the fluorescence endoscope system 30 according to this embodiment differs from the fluorescence endoscope system 20 according to the second embodiment in that it is provided with a reference light source 4b' that emits reference light, instead of the second excitation light source 4b of the light-source unit 4, and also in a ratio β stored in the autofluorescence signal setting section 5. The reference light does not excite fluorescent materials. Also, in this embodiment, instead of the fluorescence filter 10, a wavelength selective filter 10' is employed, which has different transmission bands between during observation with the excitation light and during observation with the reference light.

An element having a transmission band in the fluorescence wavelength band of the agent-fluorescence during observation with the excitation light is used as the wavelength selective filter 10'. During observation with the reference light, an element having a transmission band that does not overlap with the fluorescence wavelength band of the agent-fluorescence, for example, a Fabry-Perot type variable spectrum element, is used as the wavelength selective filter 10'

In the fluorescence endoscope system 30 according to this embodiment, a ratio β ($=I_5/I_4$) between a reflected-light intensity $I_4$ at the surface of the biological tissue, obtained when the reference light is radiated, and an autofluorescence intensity $I_5$ obtained when the excitation light is radiated is measured in advance and stored in the autofluorescence signal setting section 5. In the observation region, the ratio of the reflected-light intensity to the autofluorescence intensity is considered not to show large variations. Therefore, by multiplying the reflected-light intensity information acquired by radiating the reference light from the reference light source 4b' with the ratio β stored in advance, it is possible to estimate the autofluorescence intensity when the excitation light is radiated from the excitation light source 4a.

The operation of the thus-configured fluorescence endoscope system 30 according to this embodiment is described below.

To observe biological tissue having a fluorescent agent attached thereto or absorbed therein using the fluorescence endoscope system 30 according to this embodiment, first, the insertion section 2 is inserted into the body cavity, and the tip 2a thereof is made to face an observation site in the body cavity. In this state, excitation light and reference light are emitted from the light-source unit 4, and the excitation light and reference light propagated through the light guide 8 are radiated onto the observation site in the body cavity.

The fluorescent agent attached to or absorbed in the biological tissue is excited by irradiation with the excitation light, and agent fluorescence is produced. And the autofluorescent material is naturally contained in the biological tissue, autofluorescence is also excited by irradiation with the excitation light. This agent-fluorescence and autofluorescence light in a specific wavelength band is transmitted through the wavelength selective filter 10' and is acquired by the image-acquisition device 11. Accordingly, an image containing intensity information of the agent-fluorescence (hereinafter referred to as agent-fluorescence image information) is obtained.

On the other hand, when the reference light is radiated, only light reflected at the surface of the biological tissue is observed. This reflected light in a specific wavelength band is transmitted through the wavelength selective filter 10' and is acquired by the image-acquisition device 11. Accordingly, an image containing intensity information of the reflected light (hereinafter, reflected-light image information) is obtained.

Then, by sending the reflected-light image information obtained by the image-acquisition device 11 to the autofluorescence signal setting section 5, it is multiplied by the ratio β stored in advance, and the autofluorescence intensity information is estimated. The estimated autofluorescence intensity information is sent to the image compensation section 6.

Similarly to the first embodiment, the autofluorescence intensity information and the agent-fluorescence image information obtained by the image-acquisition device 11 are input to the image compensation section 6, where the autofluorescence intensity information is subtracted from the agent-fluorescence image information. In other words, the fluorescence image information sent from the image-acquisition device 11 contains both agent-fluorescence and autofluorescence. Therefore, in the image compensation section 6, by subtracting the autofluorescence intensity information estimated in the autofluorescence signal setting section 5, it is possible to reduce the intensity of fluorescence (background fluorescence) in regions other than the region where the agent-fluorescence is produced. Thus, with the fluorescence endoscope system 30 according to this embodiment, it is possible to improve the contrast of the image of the agent-fluorescence, and obtain a clear fluorescence image.

In this embodiment, unlike the first embodiment in which the intensity information is subtracted indiscriminately, the autofluorescence intensity information estimated on the basis of the actually obtained reflected-light image of the biological tissue is subtracted. Therefore, in this embodiment, it is possible to subtract autofluorescence intensity information in consideration of intensity variations in the image caused by the elements of the endoscope system 30, such as the light source, the optical system, and the image-acquisition device 11, as well as intensity variations in the image caused by undulations in the biological tissue or the distance from the tip 2a of the insertion section 2. As a result, there is an advantage in that it is possible to more reliably remove background fluorescence, allowing observation with a clearer agent-fluorescence image.

Figure 8:
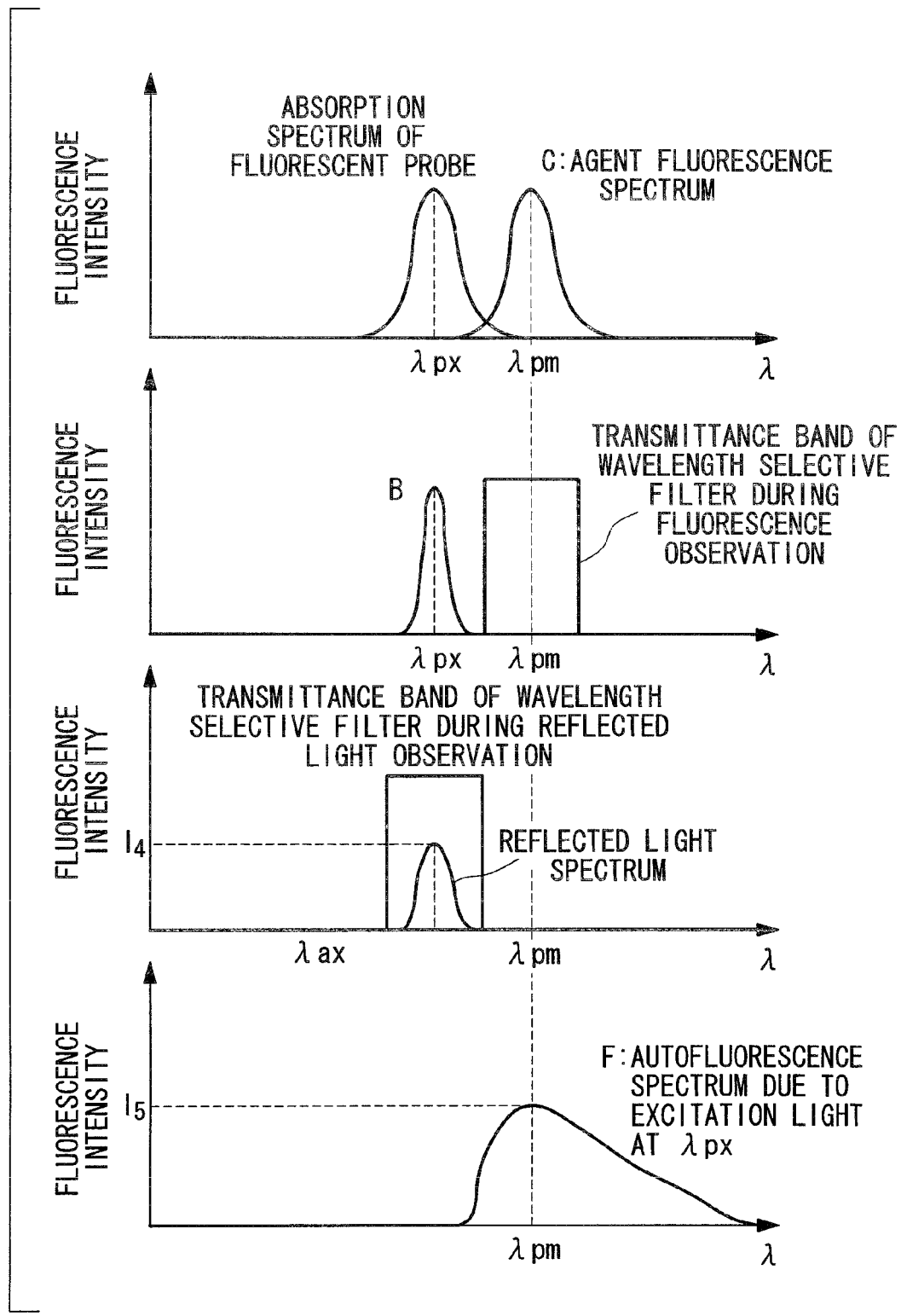
FIG. 8, which is a modification of FIG. 7, is a diagram showing wavelength characteristics in a case where an excitation light source and a reference light source are the same light source.

The reference light source 4b' used in this embodiment may be the same light source as the excitation light source 4a. In this case, as shown in FIG. 8, the wavelength band of the excitation light should be set as the transmission band of the wavelength selective filter 10'. Furthermore, it is preferable to select a band that does not depend on the blood distribution in the biological tissue, for example, a wavelength band in which the absorption by blood is weak. By doing so, it is possible to more accurately estimate the autofluorescence image.

The invention claimed is:

1. A fluorescence endoscope system for observing fluorescence from a fluorochrome attached to or absorbed in biological tissue, comprising:
    an excitation light source that emits excitation light that excites the fluorochrome;
    an image-acquisition section that acquires fluorescence emitted from the biological tissue when irradiated with the excitation light from the excitation light source;
    an autofluorescence signal setting section that sets an autofluorescence signal intensity to be emitted from the biological tissue when irradiated with the excitation light;
    an image compensation section that compensates fluorescence image information acquired by the image-acquisition section on the basis of the autofluorescence signal intensity set by the autofluorescence signal setting section;

another excitation light source that emits other excitation light in a wavelength band in which the excitation efficiency of the fluorochrome is lower as compared to the excitation efficiency of the fluorochrome with the excitation light, in a wavelength band different from the excitation light emitted from the excitation light source, wherein when the two kinds of excitation light are radiated from the two excitation light sources in an alternating manner, the image-acquisition section acquires the respective fluorescences emitted from the biological tissue, and the autofluorescence signal setting section estimates the autofluorescence signal intensity on the basis of the fluorescence image information acquired by the image-acquisition section when the other excitation light is radiated.

2. The fluorescence endoscope system according to claim 1, wherein the autofluorescence signal setting section includes an image region specifying section that specifies an image region in at least part of the fluorescence image acquired by the image-acquisition section, and a fluorescence signal intensity in the image region specified by the image region specifying section is set as the autofluorescence signal intensity.

3. The fluorescence endoscope according to claim 1, wherein the autofluorescence signal setting section estimates the autofluorescence signal intensity by multiplying the fluorescence image information acquired by radiating the other excitation light by a previously determined ratio between an autofluorescence intensity emitted from the biological tissue when irradiated with the excitation light and an autofluorescence intensity emitted from the biological tissue when irradiated with the other excitation light.

4. The fluorescence endoscope according to claim 3, wherein the fluorochrome is not dispersed.

5. A fluorescence endoscope system for observing fluorescence from a fluorochrome attached to or absorbed in biological tissue, comprising:

an excitation light source that emits excitation light that excites the fluorochrome;

an image-acquisition section that acquires fluorescence emitted from the biological tissue when irradiated with the excitation light from the excitation light source;

an autofluorescence signal setting section that sets an autofluorescence signal intensity to be emitted from the biological tissue when irradiated with the excitation light;

an image compensation section that compensates fluorescence image information acquired by the image-acquisition section on the basis of the autofluorescence signal intensity set by the autofluorescence signal setting section; and a reference light source that emits illumination light for acquiring a reflection-light image from the biological tissue;

wherein when excitation light from the excitation light source and reference light from the reference light source are radiated in an alternating manner, the image-acquisition section acquires the fluorescence emitted from the biological tissue and the reflected light of the reference light, respectively, and the autofluorescence signal setting section estimates the autofluorescence signal intensity by multiplying a reflection-light image information acquired by radiating the reference light by a previously stored ratio between a reflected-light intensity at a surface of the biological tissue, obtained when the reference light is radiated and an autofluorescence intensity obtained when the excitation light is radiated.

6. The fluorescence endoscope according to claim 5, wherein the reference light source and the excitation light source are the same light source.

* * * * *